(12) United States Patent
Wuyts et al.

(10) Patent No.: US 12,351,842 B2
(45) Date of Patent: Jul. 8, 2025

(54) *LACTOBACILLUS MUDANJIANGENSIS* STRAINS AND CELLULASE DERIVED THEREFROM

(71) Applicant: UNIVERSITEIT ANTWERPEN, Antwerp (BE)

(72) Inventors: Sander Wuyts, Antwerp (BE); Sarah Lebeer, Antwerp (BE); Tom Eilers, Borgerhout (BE)

(73) Assignee: UNIVERSITEIT ANTWERPEN, Antwerp (BE)

( * ) Notice: Subject to any disclaimer, the term of this patent is extended or adjusted under 35 U.S.C. 154(b) by 806 days.

(21) Appl. No.: 17/427,764

(22) PCT Filed: Jan. 30, 2020

(86) PCT No.: PCT/EP2020/052223
§ 371 (c)(1),
(2) Date: Aug. 2, 2021

(87) PCT Pub. No.: WO2020/157166
PCT Pub. Date: Aug. 6, 2020

(65) Prior Publication Data
US 2022/0127589 A1    Apr. 28, 2022

(30) Foreign Application Priority Data
Feb. 1, 2019 (EP) .................................. 19155022

(51) Int. Cl.
*C12N 9/42* (2006.01)
*C12N 1/20* (2006.01)
*C12P 19/14* (2006.01)
*C12R 1/225* (2006.01)

(52) U.S. Cl.
CPC ........... *C12N 9/2437* (2013.01); *C12N 1/205* (2021.05); *C12P 19/14* (2013.01); *C12Y 302/01004* (2013.01); *C12R 2001/225* (2021.05)

(58) Field of Classification Search
CPC ....... C12N 9/2437; C12N 1/205; C12P 19/14; C12Y 302/01004; C12R 2001/225; A61K 31/711; A61K 35/747; A23L 33/135
See application file for complete search history.

(56) References Cited

FOREIGN PATENT DOCUMENTS

| KR | 101752770 B1 | 6/2017 | |
|---|---|---|---|
| WO | WO-2010075529 A2 * | 7/2010 | ............. C12N 15/74 |

OTHER PUBLICATIONS

Coniferous (2022, What is Effluent from Pulp and Paper Industry?, https://theconiferous.com/blog/effluent-from-pulp-and-paper-industry/, examiner cited) {herein Coniferous} (Year: 2022).*
Gu et al. (2013, International Journal of Systematic and Evolutionary Microbiology, cited of IDS dated Nov. 9, 2021) {herein Gu} (Year: 2013).*
Moran et al. (2018, An Applied Guide to Water and Effluent Treatment Plant Design, examiner cited) {herein Moran} (Year: 2018).*
NZ_UYIG00000000.1 (https://www.ncbi.nlm.nih.gov/nuccore/1584147043?sat=48&satkey=26479569) (Year: 2019).*
NCBI:txid1296538 Schoch CL, et al. NCBI Taxonomy: a comprehensive update on curation, resources and tools. Database (Oxford). 2020: baaa062. PubMed: 32761142 PMC: PMC7408187. (Year: 2020).*
Wuyts et al. (2019, Microbial Genomics, DOI 10.1099/mgen.0.000286, cited on IDS dated Nov. 9, 2021) {herein Wuyts} (Year: 2019).*
International Search Report and Written Opinion mailed Mar. 20, 2020 in reference to co-pending European Application Application No. PCT/EP2020/052223 filed Jan. 30, 2020.
European Search Report in reference to co-pending European Application Application No. 19155022 filed Jan. 2, 2019.
Abby, et al., "Identification of protein secretion systems in bacterial genomes", Scientific Reports, pp. 1-14, 2016.
Cury, et al., "Integrative and conjugative elements and their hosts: composition, distribution and organization", Nucleic Acids Research, vol. 45, No. 15, pp. 8943-8956, 2017.
Goris, et al., "DNA-DNA hybridization values and their relationship to whole-genome sequence similarities", International Journal of Systematic and Evolutionary Microbiology, vol. 57, pp. 81-91, 2007.
Gu, et al., "*Lactobacillus mudanjiangensis* sp. nov., *Lactobacillus songhuajiangensis* sp. nov. and *Lactobacillus henjiangensis* sp. nov., isolated from Chinese traditional pickle and sourdough", International Journal of Systematic and Evolutionary Microbiology, vol. 63, pp. 4698-4706, 2013.
Guglielmini, et al., "The Repertoire of ICE in Prokaryotes Underscores the Unity, Diversity, and Ubiquity of Conjugation", PLOS Genetics, vol. 7, Issue 8, pp. 1-11, Aug. 2011.

(Continued)

*Primary Examiner* — Paul J Holland
*Assistant Examiner* — Erica Nicole Jones-Foster
(74) *Attorney, Agent, or Firm* — FRESH IP PLC; Michael Anderson

(57) ABSTRACT

The present invention in particular relates to the identification of novel *Lactobacillus mudanjiangensis* strains which are characterized in having a whole genome GC content of less than 43%. Moreover, these strains are characterized by the expression of a novel cellulase enzyme, which has numerous applications in the fields of for example agriculture, bioconversion, detergents, fermentation, food, paper industry, or textile industry.

7 Claims, 5 Drawing Sheets
Specification includes a Sequence Listing.

(56) References Cited

OTHER PUBLICATIONS

Jung, et al., "Complete Genome Sequence of Leuconostoc carnosum Strain JB16, Isolated from Kimchi", Genome Announcement, vol. 194, No. 23, pp. 6672-6673, Dec. 2012.

Liang, et al., "Isolation, Screening, and Identification of Cellulolytic Bacteria from Natural Reserves in the Subtropical Region of China and Optimization of Cellulase Production by Paenibacillus terrae ME27-1", Hindawi Publishing Corporation, vol. 2014, pp. 1-14, 2014.

Omadjela, et al., "BcsA and BcsB form the catalytically active core of bacterial cellulose synthase sufficient for in vitro cellulose synthesis", vol. 100, No. 44, PNAS, pp. 17856-17861, Oct. 29, 2013.

Wuyts, et al., "Comparitive genome analysis of Lactobacillus mudanjiangensis, an understudied member of the Lactobacillus plantarum group", pp. 1-25, Feb. 5, 2019.

Qin, et al., "Cellulase [Lactobacillus crispatus JV-Vo1]", XP002792299, Nov. 27, 2012.

* cited by examiner

LACTOBACILLUS MUDANJIANGENSIS STRAINS AND CELLULASE DERIVED THEREFROM

CROSS REFERENCES TO RELATED APPLICATIONS

This application is a national-stage application under 35 U.S.C. § 371 of International Application No. PCT/EP2020/052223, filed Jan. 30, 2020, which International Applications claims benefit of priority to European Application No. 19155022.7, filed Feb. 1, 2019.

FIELD OF THE INVENTION

The present invention in particular relates to the identification of novel *Lactobacillus mudanjiangensis* strains which are characterized in having a whole genome GC content of less than 43%. Moreover, these strains are characterized by the expression of a novel cellulase enzyme, which has numerous applications in the fields of for example agriculture, bioconversion, detergents, fermentation, food, paper industry, biocontrol, or textile industry.

BACKGROUND TO THE INVENTION

The genus *Lactobacillus* is known to be extremely diverse and consists of different phylogenetic groups that show a diversity roughly equal to the expected diversity of a typical bacterial genus. One of the most prominent phylogenetic groups within this genus is the *Lactobacillus plantarum* group which contains the understudied *Lactobacillus mudanjiangensis* species. *Lactobacillus mudanjiangensis* is a species that has been described for the first time in 2013. It was isolated from a traditional pickle fermentation in the Heilongjiang province in China (Gu et al., 2013). Since its first description, no other study has provided additional characterization or reported the isolation of other strains of the *L. mudanjiangensis* species. Therefore, currently, not a single genomic assembly of this species is publicly available. In this study, three strains classified as *L. mudanjiangensis*, were isolated from three different carrot juice fermentations and their whole-genome sequence was determined, together with the genome sequence of the type strain DSM28402$^T$. The genomes of all four strains were compared with publicly available *L. plantarum* group genome sequences. This analysis showed that *L. mudanjiangensis* harbored the second largest genome size and gene count of the whole *L. plantarum* group. In addition, all members of this species showed the presence of a gene coding for a putative cellulose-degrading enzyme. Finally, three of the four *L. mudanjiangensis* strains studied showed the presence of pili on scanning electron microscopy (SEM) images, which were linked to conjugative gene regions, coded on plasmids in at least two of the strains studied.

Since the discovery of the mucus-binding SpaCBA pili (also termed fimbriae) as main adhesins in *Lactobacillus rhamnosus* GG, several comparative genomic studies have focused on exploring similar gene clusters in other lactobacilli, including the members of the *L. plantarum* group. Whereas these specific SpaCBA pili play an important role in cell surface adhesion, pili in general can be of importance for an array of other functions as well, ranging from biofilm formation to uptake of extracellular DNA via natural competence (type IV pili) or facilitation of DNA transfer via conjugation. The latter is a process that uses conjugative pili to bring bacterial cells together and provide an interface to exchange macromolecules, such as DNA or DNA-protein complexes. In general, such a conjugation system consists of three major components, namely (i) a relaxase (MOB) that will bind and knick the DNA at the origin of replication, (ii) a coupling protein (T4CP) that will couple the relaxase-DNA complex to (iii) a type IV secretion system (T4SS), which ultimately transfers the whole complex to the recipient cell (Abby et al., 2016). Historically, these conjugation systems and their pili have been associated with conjugative plasmids only (Guglielmini et al., 2011), one of the main drivers of horizontal gene transfer (Cury et al., 2017). However, recently, also integrative and conjugative elements (ICEs), which harbor conjugation systems as well, have been found to be another important driver of horizontal gene transfer (Cury et al., 2017). Such conjugative pili and horizontal gene transfer often play a role in niche adaptation of bacteria.

In this study, the genome of the type strain of *L. mudanjiangensis* was sequenced to confirm the classification of the four identified strains. Furthermore, we aimed to provide more insights into the genomic features of this understudied species, in relation to the other members of the *L. plantarum* group and other publicly available genome sequences, and in relation to fermentation of plant polysaccharides, using a comparative genomics approach. The genome sequences were used to screen for *L. mudanjiangensis* species-specific properties, which included an analysis for the presence of genes related to pili formation and conjugation. In total, 304 genomes were subjected to an in-depth analysis focusing on the phylogenetic relationships as well as the predicted functional capacity of these strains.

SUMMARY OF THE INVENTION

As already detailed herein above, the novel strains showed the presence of a gene coding for a putative polysaccharide-degrading enzyme, more in particular a cellulose-degrading enzyme.

Hence, in a first aspect, the present invention provides an isolated, recombinant or synthetic nucleic acid molecule (encoding such cellulase); more in particular comprising a nucleotide sequence having at least 70%, in particular at least 85%, even more in particular at least 90%, 95% or 99% sequence identity/homology to SEQ ID N° 1.

In a specific embodiment of the nucleotide sequence of the present invention encodes a polypeptide having cellulase activity and comprises an amino acid sequence having at least 70%, in particular at least 85%, even more in particular at least 90%, 95% of 99% sequence identity/homology to SEQ ID N° 2; or an enzymatically active fragment thereof.

The present invention also provides a polypeptide having cellulase activity; said polypeptide comprising an amino acid sequence having at least 70%, in particular at least 85%, even more in particular at least 90%, 95% of 99% sequence identity/homology to SEQ ID N° 2; or an enzymatically active fragment thereof.

In a further aspect, the present invention provides the use of a polypeptide or enzymatically active fragment thereof, as defined herein; in agriculture, in bioconversion, as a detergent, in fermentation, in food, in the paper industry, in the textile industry, or as a human or veterinary postbiotic.

The present invention further provides an isolated bacterial strain of the *Lactobacillus mudanjiangensis* species comprising a nucleic acid molecule and/or a polypeptide as defined herein; more in particular, said *Lactobacillus mudanjiangensis* species may be characterized by having a whole genome GC content of less than 43%.

The present invention further provides an isolated bacterial strain of the *Lactobacillus mudanjiangensis* species deposited as *Lactobacillus mudanjiangensis* AMBF249 under accession number LMG P-31215 (deposited at BCCM on Jan. 15, 2019) or a strain having at least 95% sequence identity/homology (such as sequence/average nucleotide identity (ANI)) thereto; more in particular, said *Lactobacillus mudanjiangensis* species may be characterized by a whole genome GC content of less than 43%.

Furthermore, the present invention provides a composition comprising a bacterial strain as defined herein.

The present invention also provides the isolated bacterial strain or the composition as defined herein for use in human or veterinary medicine.

In a further embodiment, the present invention provides the use of an isolated bacterial strain of the *Lactobacillus mudanjiangensis* species or a composition as defined herein; in agriculture, in bioconversion, in fermentation, as a biocontrol agent, as a detergent, in food, in the paper industry, in the textile industry, or as a human or veterinary probiotic, or pharmabiotic.

The present invention further provides an isolated deposited bacterial strain of the *Lactobacillus mudanjiangensis* species; or strains having at least 95% sequence identity thereto; or a composition comprising such isolated bacterial strain for use in human or veterinary medicine.

Finally, the present invention provides the use of the isolated deposited bacterial strain of the *Lactobacillus mudanjiangensis* species; or strains having at least 95% sequence identity thereto; or a composition comprising such isolated bacterial strain; in agriculture, in bioconversion, in fermentation, as a detergent, in food, in the paper industry, in the textile industry or as a human or veterinary probiotic.

BRIEF DESCRIPTION OF THE DRAWINGS

With specific reference now to the figures, it is stressed that the particulars shown are by way of example and for purposes of illustrative discussion of the different embodiments of the present invention only. They are presented in the cause of providing what is believed to be the most useful and readily description of the principles and conceptual aspects of the invention. In this regard no attempt is made to show structural details of the invention in more detail than is necessary for a fundamental understanding of the invention. The description taken with the drawings making apparent to those skilled in the art how the several forms of the invention may be embodied in practice.

DETAILED DESCRIPTION OF THE INVENTION

Figure 1:
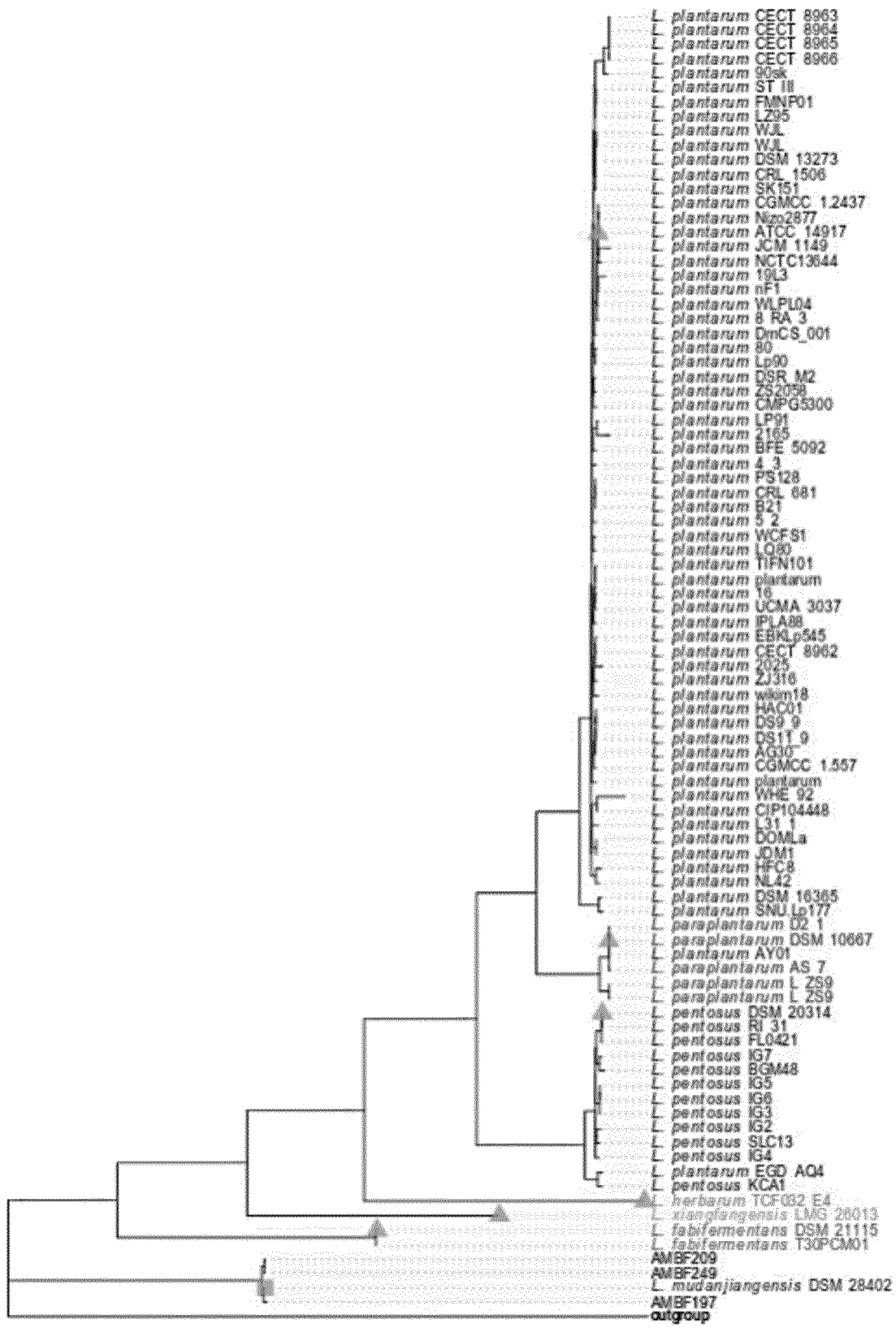
FIG. 1: Part of the Maximum likelihood phylogenetic tree of the *Lactobacillus plantarum* group, based on the amino acid sequences of 612 single-copy marker genes. *Lactobacillus algidus* DSM 15638 was used as an outgroup. The branch length of the outgroup was shortened for better visualization. Type strains of each species are annotated with a triangle (NCBI) or a square (sequenced herein).

In this study, the genome sequence of the *L. mudanjiangensis* type strain DSM $28402^T$ was presented together with the genomes of three new *L. mudanjiangensis* strains, AMBF197, AMBF209 and AMBF249, which were isolated from three different spontaneous carrot juice fermentations. Since previous phylogenetic analysis of this species, using the 16S rRNA, pheS, and rpoA genes, showed a close genetic relatedness with the members of the *L. plantarum* group (Gu et al., 2013), it was decided to study these genomes in relation to the closely related members of the *L. plantarum* group with a comparative genomics approach. A maximum likelihood phylogenetic tree confirmed that *L. mudanjiangensis* was closely related to all other *L. plantarum* group members. Furthermore, pairwise ANI analysis confirmed that the three strains isolated from carrot juice fermentations were members of the *L. mudanjiangensis* species.

The estimated genome size of *L. mudanjiangensis* was the second largest of the whole *L. plantarum* group found up to now. The same trend was found for the gene count per species. This means that *L. mudanjiangensis* harbored one of the largest genomes of the whole LGC, since *L. plantarum* and especially *L. pentosus* are known to be among the lactobacilli with the largest genome size and gene counts. For *L. plantarum*, this large genome and also its pangenome size have been coupled to a nomadic lifestyle. This lifestyle comes with a high genetic diversity, which is associated to the possibility to survive and thrive in many different ecosystems. This could possibly also be applied to *L. mudanjiangensis*, supported by the fact that *L. mudanjiangensis* showed a slightly larger number of Glycosyl Hydrolases (GH) than *L. plantarum*, indicating that this species is capable of transforming and metabolizing a broad spectrum of carbohydrate sources. This observation was confirmed by the fact that the type strain was found to be capable of producing organic acids from at least 21 different carbon sources (Gu et al., 2013).

Furthermore, here, a putative polysaccharide-degrading enzyme, more specifically a cellulose-degrading enzyme, annotated as endoglucanase E1, was found in all four *L. mudanjiangensis* strains, which was not found in any other LGC genome so far. Moreover, cellulose-degrading enzymes were only very exceptionally found in beneficial or food-grade lactic acid bacteria (LAB) up to now. Cellulose is the most abundant organic polymer on earth, the most important skeletal component in plants in general and the most abundant crude fiber in carrots. *Lactobacillus mudanjiangensis*' putative capability to degrade this fiber into glucose might allow members of this species to survive in many different plant-related ecosystems. Fermented carrot juices and fermented pickles are examples of such ecosystems, where three and one of the strains studied were isolated from, respectively. Together, these results suggested that, similar to *L. plantarum*, a nomadic or otherwise a plant-adapted lifestyle could be assigned to *L. mudanjiangensis*. Moreover, the activity of the cellulase was experimentally tested and shown to degrade carboxymethylcellulose.

Hence, in a first aspect, the present invention provides an isolated, recombinant or synthetic nucleic acid molecule comprising a nucleotide sequence having at least 70%, in particular at least 85%, even more in particular at least 90%, 95% or 99% sequence identity/homology to SEQ ID N° 1. Said gene sequence corresponding to said novel cellulose-degrading gene. Accordingly, the present invention provides an isolated, recombinant or synthetic nucleic acid molecule comprising a nucleotide sequence having at least 95% sequence identity to SEQ ID N° 1, and encoding a polypeptide having cellulase activity.

In a specific embodiment, the nucleotide sequence of the present invention encodes a polypeptide having cellulase activity and comprises an amino acid sequence having at least 70%, in particular at least 85%, even more in particular at least 90%, 95% or 99% sequence identity/homology to SEQ ID N° 2; or an enzymatically active fragment thereof. Said amino acid sequence corresponding to said novel cellulose-degrading enzyme. Specifically, said nucleotide sequence may encode an enzymatically active fragment of a polypeptide comprising an amino acid sequence having at least 95% sequence identity to SEQ ID N° 2.

Where in the context of the present invention, the term sequence identity or sequence homology is used, this is meant to be calculated across the whole reference sequence and not over shorter fragments thereof.

The present invention further provides a polypeptide having cellulase activity; said polypeptide comprising an amino acid sequence having at least 95% sequence identity to SEQ ID N° 2. Furthermore, the present invention provides an enzymatically active fragment of a polypeptide comprising an amino acid sequence having at least 95% sequence identity to SEQ ID N° 2; said fragment having cellulase activity.

In the context of the present invention the term "cellulase" is meant to be an enzyme capable of degrading cellulose to glucose. For commercial purposes, this enzyme is currently often produced using fungi, such as from the *Trichoderma* or *Deuteromycota* genus, however, the present invention provides a novel (bacterial) source for such enzymes, namely the *Lactobacillus mudanjiangensis* species.

Since cellulose is one of the most abundant organic polymers on earth and being a crucial skeletal component in plants, this novel cellulose-degrading enzyme and *Lactobacillus mudanjiangensis* species expressing it, may have numerous applications, of which only some include: agriculture, bioconversion, detergents, fermentation, biocontrol, food industry, paper industry, textile industry, . . . ; wherein the *Lactobacillus mudanjiangensis* species themselves, may also be used as human or veterinary probiotics; or wherein the polypeptides or enzymatically active fragments thereof may be used as a human or veterinary postbiotic, or pharmabiotic.

In the context of the present invention, the term "postbiotic" refers to a metabolic byproduct or (such as cellulase) or inactivated/inanimate formulation obtainable from a probiotic bacterial strain, having still a probiotic function. Such postbiotics seem to be responsible for many of the beneficial effects of the probiotics themselves. In the context of the present invention, the term "pharmabiotic" refers to a health-promoting agent.

Hence, the present invention provides the use of a polypeptide or enzymatically active fragment thereof, as disclosed herein, as well as of an isolated bacterial strain of the *Lactobacillus mudanjiangensis* species or a composition comprising such strains; in agriculture, in bioconversion, in fermentation, in biocontrol, in food, in the paper industry, in the textile industry, or as a human or veterinary probiotic. More in particular, the present invention provides the use of the deposited isolated bacterial strain of the *Lactobacillus mudanjiangensis* species or strains having at least 94%, or alternatively 95% sequence identity/homology thereof; or a composition comprising such isolated bacterial strain; in agriculture, in bioconversion, in fermentation, in biocontrol, in food, in the paper industry, in the textile industry or as a human or veterinary probiotic.

More specific applications for each of these industries may be identified as follows:

Agriculture—For Example: Plant pathogen and disease control; generation of plant and fungal protoplasts; enhanced seed germination and improved root system; enhanced plant growth and flowering; improved soil quality; reduced dependence on mineral fertilizers Bioconversion—For Example: Conversion of cellulosic materials to ethanol, other solvents, organic acids and single cell protein, and lipids; production of energy-rich animal feed; improved nutritional quality of animal feed; improved ruminant performance; improved feed digestion and absorption; preservation of high-quality fodder Detergent—For Example: Cellulase-based detergents; superior cleaning action without damaging fibers; improved color brightness and dirt removal; remove of rough protuberances in cotton fabrics; anti-redeposition of ink particles Fermentation—For Example: Improved malting and mashing; improved pressing and color extraction of grapes; improved aroma of wines; improved primary fermentation and quality of beer; improved viscosity and filterability of wort; improved must clarification in wine production; improved filtration rate and wine stability Food Industry—For Example: Release of the antioxidants from fruit and vegetable pomace; improvement of yields in starch and protein extraction; improved maceration, pressing, and color extraction of fruits and vegetables; clarification of fruit juices; improved texture and quality of bakery products; improved viscosity fruit purees; improved texture, flavor, aroma, and volatile properties of fruits and vegetables; controlled bitterness of citrus fruits Paper Industry—For Example: Coadditive in pulp bleaching; biomechanical pulping; improved draining; enzymatic de-inking; reduced energy requirement; reduced chlorine requirement; improved fiber brightness, strength properties, and pulp freeness and cleanliness; improved drainage in paper mills; production of biodegradable cardboard, paper towels, and sanitary paper Textile Industry—For Example: Biostoning of jeans; biopolishing of textile fibers; improved fabrics quality; improved absorbance property of fibers; softening of garments; improved stability of cellulosic fabrics; removal of excess dye from fabrics; restoration of color brightness Biocontrol: Conferring a health benefit to the plant by inhibiting a pathogenic microbe or stimulate innate immune responses or promoting plant growth Further potential applications—For example: Improved carotenoids extraction; improved oxidation and colour stability of carotenoids; improved olive oil extraction; improved malaxation of olive paste; improved quality of olive oil; reduced risk of biomass waste; production of hybrid molecules; production of designer cellulosomes Moreover, the present invention further provides an isolated bacterial strain of the *Lactobacillus mudanjiangensis* species; or a composition comprising such isolated bacterial strain for use in human or veterinary medicine. More in particular, the present invention provides the isolated deposited bacterial strain of the *Lactobacillus mudanjiangensis* species as defined herein, or a strain having at least 94%, or alternatively 95% sequence identity/homology thereof; or a composition comprising such isolated bacterial strain for use in human or veterinary medicine. Specifically, said strains comprise a cellulase gene having at least 95% sequence identity to the cellulase gene of the *Lactobacillus mudanjiangensis* strains as defined herein.

The present invention further provides an isolated bacterial strain of the *Lactobacillus mudanjiangensis* species comprising a nucleic acid molecule and/or a polypeptide as defined herein; more in particular, said *Lactobacillus mudanjiangensis* species may be characterized by having a whole genome GC content of less than 43%.

As detailed above, the *Lactobacillus mudanjiangensis* type strain was initially identified in China in 2013 (Gu et al., 2013). While, at that time, the GC content of this strain was estimated to be about 45.1 mol % based on thermal melting protocols, no full genome sequencing of this strain was performed at that time. The current inventors have for the first time fully sequenced the genome of this strain, and accurately determined its GC content as being 43.06%. The *Lactobacillus mudanjiangensis* species of the present invention are characterized in having a GC content of less than 43%, namely AMBF197 (42,85%), AMBF209 (42.73%) and AMBF249 (42.83%). Moreover, the *Lactobacillus mudanjiangensis* species of the present invention further differ from the Chinese *Lactobacillus mudanjiangensis* type strain in having a longer 16S rRNA sequence. All 3 strains of the present invention have a 16S rRNA sequence of 1571 basepairs compared to only 1458 basepairs for the Chinese type strain.

The present invention further provides an isolated bacterial strain of the *Lactobacillus mudanjiangensis* species deposited as *Lactobacillus mudanjiangensis* AMBF249 under accession number LMG P-31215 (deposited at BCCM on Jan. 15, 2019) or a strain having at least 95% sequence identity thereto; more in particular, said *Lactobacillus mudanjiangensis* species may be characterized by a whole genome GC content of less than 43%. Specifically, said strains comprise a cellulase gene having at least 95% sequence identity to the cellulase gene of a *Lactobacillus mudanjiangensis* AMBF249 strain.

Moreover, it was found that some of the identified *Lactobacillus mudanjiangensis* species are further characterized in comprising a conjugative plasmid, predicted to encode functions that promote survival and adaptation in fermented vegetable. This would render the strains highly suitable for use as a starter culture, moreover, the plasmid itself could have further applications in the field of microbiology.

Conjugation is one of the main drivers of horizontal gene transfer and is commonly associated with conjugative plasmids (Cury et al., 2017). Here, two of the five conjugative regions found were plasmid-associated and the two plasmids found were exactly the same for both *L. mudanjiangensis* AMBF209 and AMBF249, although these strains were isolated from different household carrot juice fermentations (HF08 and HF27, respectively). Previous studies also identified and described conjugative plasmids in other *Lactobacillus* species, such as *Lactobacillus brevis, Lactobacillus casei, Lactobacillus gasseri, Lactobacillus hokkaidonensis, L. plantarum* and *Lactobacillus reuteri*. Genes on these plasmids often code for proteins involved in detoxification, virulence, antibiotic resistance and ecological interactions, which could give them a fitness advantage in certain environments. Here, apart from the conjugation-related genes, many genes were annotated as hypothetical proteins on the conjugative plasmid. However, since this plasmid showed great similarity with a plasmid from a *Leuconostoc* strain, which was isolated from fermented kimchi (Jung et al., 2012), it could potentially harbor genes that are beneficial for survival on plants or in a fermented vegetable environment. In that respect, it was found that strains harboring this predicted conjugative plasmid (*L. mudanjiangensis* AMBF209 and AMBF249) expressed a higher level of gentamycin resistance, compared to the other two strains lacking the plasmid (*L. mudanjiangensis* AMBF197 and DSM 28402$^T$).

Furthermore, SEM analysis revealed the presence of pili or fimbriae in three of the four *L. mudanjiangensis* strains studied. In this study, the observation of pili in *L. mudanjiangensis* was associated with bacterial conjugation. Three of the four strains were found to carry at least one complete putative conjugation region, including a gene that possibly codes for a VirB2 homolog, the major subunit of a conjugation-related pilus. The three strains that harbored this conjugation region all showed pili formation on the SEM images, whereas this was not the case for strain AMBF197, which lacked this region. These results suggested that the detected pili might play a role in cell to cell contact during the conjugation process, although this was not yet experimentally validated.

Finally, the putative cellulase activity was tested enzymatically. These tests showed that the three new *L. mudanjiangensis* strains (AMBF197, AMBF209 and AMBF249) as discussed herein above, have cellulase activity. A carboxymethyl cellulose assay allowed semi-quantitative determination of the cellulose-degrading activity and proved the cellulose degrading activity of the three novel *L. mudanjiangensis* strains, whereas the prior art identified *L. mudanjiangensis* strain (DSM 28402$^T$) did not show this activity. To confirm that this activity resulted from the aforementioned genes, heterologous expression in *Escherichia coli* was performed.

EXAMPLES

Materials And Methods

Sequencing of the *Lactobacillus mudanjiangensis* Type Strain and Downloading of Publicly available Assemblies The type strain of *L. mudanjiangensis* [*L. mudanjiangensis* DSM 28402$^T$ (=LMG 27194$^T$=CCUG 62991$^T$)] was purchased from a public microorganism collection (BCCM-LMG, Ghent, Belgium). The strain was grown overnight in de Man-Rogosa-Sharpe (MRS) medium (Carl Roth, Karlsruhe, Germany) and DNA was extracted using the NucleoSpin 96 tissue kit (Macherey-Nagel, Düren, Germany), with an extra cell lysis step using 20 mg/mL of lysozyme (Sigma-Aldrich, St. Louis, M.O., USA) and 100 U/mL of mutanolysin (Sigma-Aldrich). Whole-genome sequencing was performed using the Nextera XT DNA Sample Preparation kit (Illumina, San Diego, C.A., USA) and the Illumina MiSeq platform, using 2×250 cycles, at the Laboratory of Medical Microbiology (University of Antwerp, Antwerp, Belgium). Assembly of the genome sequence was performed using SPAdes v 3.12.0. In addition, all genome sequences annotated as putative *L. mudanjiangensis* were added to this analysis. Finally, all genome sequences annotated as *L. fabifermentans, L. herbarum, L. paraplantarum, L. pentosus, L. plantarum* and *L. xiangfangensis* were downloaded from the National Center for Biotechnology Information (NCBI) Assembly database on 24 Jul. 2018, using in-house scripts. In total, 310 genomes were used as an input for quality control.

Quality Control and Annotation

Basic genome characteristics, including genome size, GC content and the N50 value, were estimated using Quast 4.6.3. The quality of the genome assemblies was evaluated using the Quast output. After visualization of several quality control parameters using ggplot2, genomes with a N50 value <25,000 bp and a number of undefined nucleotides (N) per 100,000 bases >500 were discarded. A total of 304 assemblies passed the quality control, among which a genome sequence for the type strain of *L. mudanjiangensis* and three of the four fermented carrot juice strains putatively classified as *L. mudanjiangensis*. Finally, Prokka 1.12 was used to predict and annotate genes for all genome sequences. In addition to its internal databases, a customized genus-specific BLAST database was used for higher quality annotation with Prokka's-usegenus option. This database was created using BLAST and all complete *Lactobacillus* genomes found in the NCBI Assembly database.

Defining the Pangenomes of all *Lactobacillus plantarum* Group Species

To define the pangenome, all genes were clustered into orthogroups using OrthoFinder 2.2.6 and further analyzed in R (R Core Team, 2015). Here, a core orthogroup is defined as an orthogroup present in more than 95% of a set of genomes. All other orthogroups are defined as accessory orthogroups. An upset plot was created using the R package UpSetR. Unique orthogroups belonging to *L. mudanjiangensis* were further annotated using EggNOG-mapper and visualized using ggplot2.

Phylogenetic Tree Construction

Single-copy core orthogroups found by Orthofinder were used as input for the construction of a phylogenetic tree. *Lactobacillus algidus* DSM 15638 (NCBI Assembly accession number GCA_001434695) served as an outgroup, as it is the species most closely related to the *L. plantarum* group. The first protein sequence of each fasta file of the single-copy core orthogroups was compared with a BLAST database of all genome proteins of the outgroup's genome sequence. All hits with a coverage >75% and a percentage similarity >50% were added to the alignment of each orthogroup. These alignments, on amino acid level, were concatenated into a supermatrix that was used in RaxML 8.2.9, to build a maximum likelihood phylogenetic tree with the—a option, which combines a rapid bootstrap algorithm with an extensive search of the tree space, starting from multiple different starting trees. The tree and subtrees were plotted with the R package ggtree.

Average Nucleotide Identity

All pairwise average nucleotide identity (ANI) values were calculated with the Python pyani package, using a BLASTN approach based on the methodology described by Goris et al. (2007).

Plasmid Identification

Detection and reconstruction of plasmids in the different *L. mudanjiangensis* strains was performed using Recycler v0.7, with the original fastq files and SPAdes assembly graphs as input. The assembled plasmids were annotated with Prokka and further characterized by scanning against the EggNOG database, as described above. The presence of a conjugation system was confirmed with CONJScan, as described above. The percentage identity between the different plasmids found was assessed using BLAST. The similarity with any previously described plasmid was checked by performing a BLAST search against the NCBI nucleotide (nt) database. A plasmid map was created using Geneious v8.

Delimitation of Integrative and Conjugative Elements

The presence of ICEs was explored by a similar approach as the pipeline described previously (Cury et al., 2017). Briefly, all strict core genes, i.e. genes present in all strains of *L. mudanjiangensis* were found using the Orthofinder output (see above). Next, all flanking core genes of each conjugative region were identified. Since within one species an ICE is expected to be found between the same core orthogroups, the flanking core genes of each conjugative region found were evaluated to determine whether or not it could be defined as an ICE.

Scanning Electron Microscopy

To assess the presence or absence of pili or fimbriae on the cell surface of *L. mudanjiangensis* strains AMBF197, AMBF209, AMBF249 and DSM 28402$^T$, scanning electron microscopy (SEM) was performed. To this end, the bacterial strains were grown overnight (MRS medium, 37° C.), gently washed with phosphate-buffered saline (per liter: 56 g of NaCl, 1.4 g of KCl, 10.48 g of $Na_2HPO_4$, 1.68 g of $KH_2PO_4$; pH 7.4) and spotted on a gold-coated membrane [(approximately $5 \times 10^7$ colony forming units (CFU) per membrane]. Bacterial spots were fixed with 2.5% (m/v) glutaraldehyde in 0.1 M sodium cacodylate buffer (2.5% glutaraldehyde, 0.1 M sodium cacodylate, 0.05% $CaCl_2.2H_2O$; pH 7.4) by gently shaking the membrane for 1 h at room temperature, followed by a further overnight fixation at 4° C. After fixation, the membranes were washed three times for 20 min with cacodylate buffer (containing 7.5% [m/v] saccharose). Subsequently, the bacteria were dehydrated in an ascending series of ethanol (50%, 70%, 90% and 95%, each for 30 min at room temperature and 100% for 2×1 h and 1×30 min) and dried in a Leica EM CPD030 (Leica Microsystems Belgium, Diegem, Belgium). The membranes were mounted on a stub and coated with 5 nm of carbon (Leica Microsystems Belgium) in a Leica EM Ace 600 coater (Leica Microsystems Belgium). SEM imaging was performed using a Quanta FEG250 SEM system (Thermo Fisher, Asse, Belgium) at the Antwerp Centre for Advanced Microscopy (ACAM, University of Antwerp) and Electron Microscopy for Material Science group (EMAT, University of Antwerp).

Detection of Genomic Clusters Encoding Pili or Fimbriae

To screen for the presence of the spaCBA gene cluster, the gene cluster that is responsible for expression of the fimbriae in *L. rhamnosus* GG, a BLAST search on protein level was performed against a BLAST database constructed for each genome separately. The gene sequences of spaA (NCBI GenBank accession number BAI40953.1), spaB (BAI40954.1) and spaC (BAI40955.1) were used as queries. Furthermore, the genomes were screened for genes encoding pili-related protein secretion systems, using the predicted amino acid sequences as query and the TXSScan definitions and profile models (Abby et al., 2016) as references in MacSyFinder v1.0.5. As only genes related to conjugation systems were found, all protein sequences of all genomes were again scanned, this time using the CONJScan definitions and profile models (Cury et al., 2017; Guglielmini et al., 2011) using MacSyFinder. In brief, a conjugation region was only considered if the conjugation genes were separated by less than 31 genes, except for genes encoding relaxases that can be separated by maximal 60 genes. The region was considered conjugative when it contained genes coding for (i) a VirB4/TraU homolog, (ii) a relaxase, (iii) a type 4 coupling protein (T4CP) and (iv) a minimum number of mating-pair formation (MPF) type-specific genes (Cury et al., 2017). For both scans, hits with alignments covering >50% of the protein profile and with an independent E-value<$10^{-3}$ were kept for further analysis (default parameters) in R (R Core Team, 2015). Conserved domain analysis of genes of interest was performed using the NCBI Conserved Domain web interface The gene regions were visualized using the R package gggenes.

Accession Number(s) and Data Availability

Sequencing data and genome assemblies are available at the European Nucleotide Archive under the accession number ERP111972.

Heterologous Expression of the Putative Cellulose Degrading Enzyme in *E. coli*

The sequence SEQ ID N° 2 was expressed heterologous in *E. coli* BL21(DE3)pLysS using the plasmid synthesis service of GeneArt™ Gene Synthesis (ThermoFisher™, Germany). An IPTG inducible plasmid is used. After heat shock transformation, the plasmid was confirmed using Sanger sequencing and SDS-PAGE. To express the protein, different temperatures (25° C. and 37° C.) and induction times ($OD_{600}$ of 0.3 and 0.8) were used before induction with IPTG (Sigma-Aldrich, Diegem, Belgium). After overnight induction production, the cells were treated as discussed in the next paragraph.

Testing for Carboxymethyl Cellulose Activity

Cellulase activity was measured using plate assay containing carboxymethyl cellulose (CMC), a compound that will be degraded by an endoglucanase (Liang et al., 2014). The different strains were grown at 30° C. in MRS. Different conditions were tested on the CMC agar containing CMC (Carl Roth GmbH, Karlsruhe, Germany); $NaNO_3$ (Sigma-Aldrich, Diegem, Belgium), $K_2HPO_4$ (Sigma-Aldrich, Diegem, Belgium), KCl (Sigma-Aldrich, Diegem, Belgium), $MgSO_4$ (Sigma-Aldrich, Diegem, Belgium), Yeast extract (VWR International, Leuven, Belgium), Bacteriological Agar(Sigma-Aldrich, Diegem, Belgium).

For the *Lactobacillus plantarum* WCFS1 and *L. mudanjiangensis* strains:
1. Concentrated overnight culture (10× concentrated at 4000×g at 4° C.),
2. Cell free supernatant: Using overnight culture, the supernatant was extracted after centrifugation at 4000× g at 4° C. and was sterilized. The pH of the *Lactobacillus* supernatant was measured.
3. Cell free supernatant corrected for pH: Condition for the supernatant of the *E. coli* that expressed the cellulase. Supernatant was corrected to the average pH of the *Lactobacillus* pH (pH=4.0)
4. Lysed cells: After production of cellulase by *E. coli*, or after overnight culture of *Lactobacillus* spp., The cells were lysed by freeze thawing followed by sonification. After centrifuging at 10,000×g for 10 minutes, the supernatant containing the intracellular proteins were extracted
5. Lysed cells corrected for pH: The pH of the supernatant containing the intracellular protein of condition 4 was corrected to a pH of 4.0.

The aforementioned conditions were added to the CMC agar and incubated at 37° C. for 48h. Afterwards, the plates were stained with 0.1% Congo Red (Carl Roth GmbH, Karlsruhe, Germany) for 30 minutes, washed by 1 M NaCl for 15 minutes twice, subsequently, 0.1% acetic acid (CHEM LAB, Zedelgem, Belgium) was added. When cellulase activity is present, Congo Red is unable to bind to the agar, leaving a clear spot on the plate. To relatively quantify the activity, the diameter of the spot was measured.

Results

The genome assembly of the type strain *L. mudanjiangensis* DSM 28402$^T$ was analyzed together with the genome sequences of three of four putative *L. mudanjiangensis* strains isolated from carrot juice fermentations, namely AMBF197, AMBF209 and AMBF249, to confirm their putative classification as *L. mudanjiangensis* members. The genome sequence of the fourth strain, *L. mudanjiangensis* AMBF198, was discarded due to stricter quality control parameters.

Furthermore, to allow comparison with other closely related *Lactobacillus* species and detection of *L. mudanjiangensis* species-specific properties, all publicly available genome sequences (NCBI Assembly database, 24 Jul. 2018) of *L. plantarum* group members were included in this comparative genomics study, totaling the number of genomes analyzed to 304.

Phylogeny of the *Lactobacillus plantarum* Group

To obtain a detailed view on the phylogeny of *L. mudanjiangensis* in relationship to the whole *L. plantarum* group, a maximum likelihood phylogenetic tree was constructed, based on 612 single-copy core orthogroups, found with Orthofinder, of which the most relevant part in respect of this application may be found in FIG. 1. The resulting topology of this tree showed seven major clades, mostly following the species annotation as described in the NCBI Assembly database. However, these results exposed a few wrongly annotated genomic assemblies. For example, both *L. plantarum* MPL16 and *L. plantarum* AY01 were annotated as *L. plantarum* before, whereas here, they were found within a Glade that contained the *L. paraplantarum* type strain. Similarly, *L. plantarum* EGD-AQ4 was found within the Glade of the *L. pentosus* type strain, whereas it was annotated as *L. plantarum* before.

As evident from FIG. 1, the type strain of *L. mudanjiangensis* formed a separate Glade together with the strains AMBF197, AMBF209 and AMBF249. Based on its single-copy core orthogroups, this species was phylogenetically the most distant to *L. plantarum*, whereas its closest relative was *L. fabifermentans*, followed by *L. xiangfangensis*.

Low Intraclade ANI Values for *Lactobacillus pentosus* and *Lactobacillus plantarum*

Figure 2:
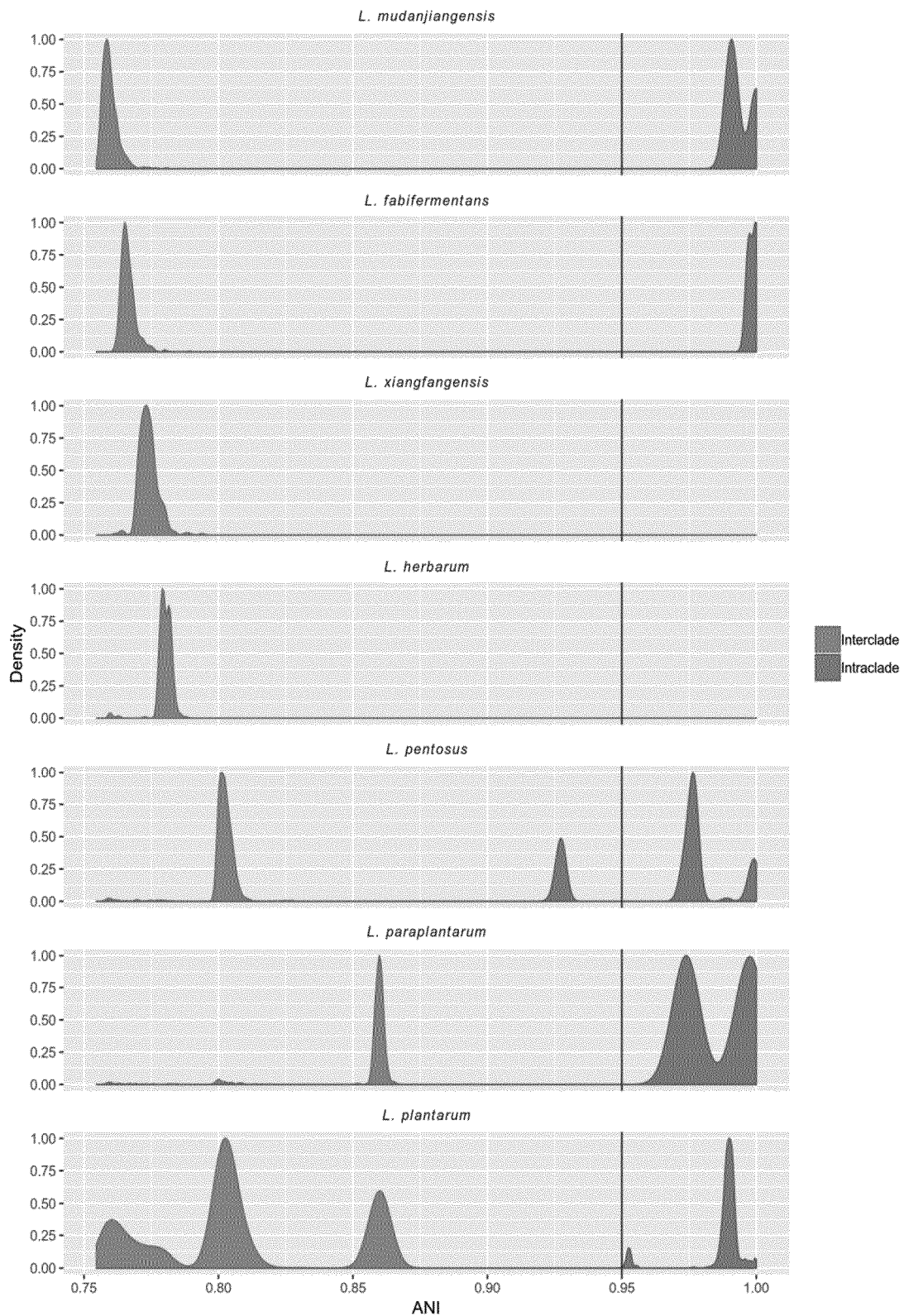
FIG. 2: Density plot of all pairwise average nucleotide identity (ANI) comparisons for each *Lactobacillus plantarum* group species. In green all interclade comparisons are shown, whereas orange shows all intraclade comparisons. For *Lactobacillus xiangfangensis* and *Lactobacillus herbarum*, no intraclade comparisons could be performed, as only one genome assembly was available for these species.

To confirm that each major phylogenetic Glade represented at least one different species, the pairwise ANI values of all genome assemblies were calculated (FIG. 2). Intraclade ANI values all exceeded the commonly used 95% species level threshold for *L. mudanjiangensis* (99.0-99.4%), *L. fabifermentans* (99.7-99.9%) and *L. paraplantarum* (99.7-99.9%), whereas their interclade ANI values were far below this threshold, showing that these clades all represented a single species. However, this was not the case for L. pentosus, for which multiple pairwise comparisons led to intraclade ANI values below this threshold, suggesting that this phylogenetic clade contained at least two species (FIG. 2). This result was also found for some L. plantarum assemblies, although to a much lesser extent, compared to L. pentosus. Therefore, it was decided that, for subsequent analyses, L. plantarum was kept as one species, whereas L. pentosus was split into two groups, each representing one species. One species was designated as species L. pentosus, represented by a Glade containing twelve genomic assemblies, including the type strain L. pentosus DSM 20314[1]. The other species, here referred to as Glade 5a, was represented by two genomic assemblies (L. pentosus KCA1 and L. plantarum EGD-AQ4) (FIG. 2). Finally, for L. xiangfangensis and L. herbarum, no intraclade comparisons could be performed, as only one genome assembly was available for these species.

Genomic Features of Lactobacillus mudanjiangensis

Our results confirmed that strains AMBF197, AMBF209 and AMBF249 were members of the L. mudanjiangensis species. Therefore, here, the first four genomes of this species were presented. Their genome size varied between 3.4 Mb (strain DSM 28402$^T$) and 3.6 Mb (strain AMBF209), whereas their GC content varied between 42.73% (strain AMBF209) and 43.06% (strain DSM 28402$^T$) Finally, a high number of transfer RNA (tRNA) genes were found in all four strains (Table 1).

TABLE 1

Genome characteristics of Lactobacillus mudanjiangensis strains.

| Genome | Total length (bp) | GC content (%) | # Coding sequences | # tRNA genes |
|---|---|---|---|---|
| AMBF197 | 3,501,388 | 42.85 | 3,463 | 65 |
| AMBF209 | 3,589,692 | 42.73 | 3,586 | 63 |
| AMBF249 | 3,554,025 | 42.83 | 3,503 | 71 |
| DSM 28402 | 3,389,962 | 43.06 | 3,346 | 66 |

From the above table, it is evident that the novel Lactobacillus mudanjiangensis strains (AMBF197, AMBF209, AMBF249) from the present invention differ from the type strain (DSM 28402) in multiple aspects such as having a total genomic length of above 3,500,000 bp and having a GC content of less than 43%.

Figure 3:
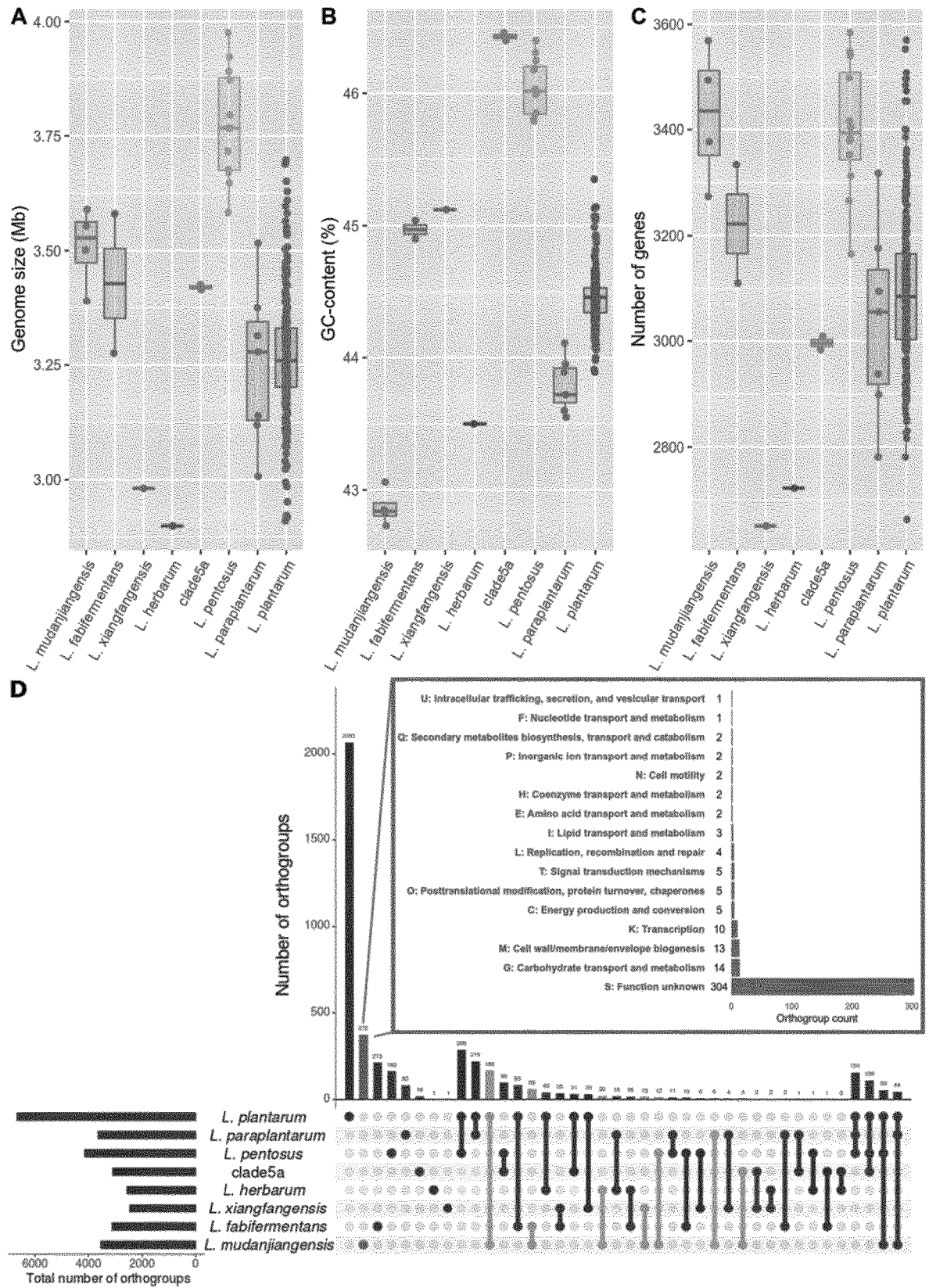
FIG. 3: Estimated genome sizes, GC contents and gene counts of all genomes of *Lactobacillus plantarum* group species studied and predicted functional capacity of all unique *Lactobacillus mudanjiangensis* orthogroups. (A) Total genome size, (B) GC content and (C) gene counts of all genomes studied, colored by species. (D) Upset plot comparing shared orthogroup counts between the eight *L. plantarum* group species. The inset shows the functional category for *L. mudanjiangensis* based on EggNOG classification.

A substantial difference in total genome length between the different species of the L. plantarum group was found (FIG. 3A). Lactobacillus mudanjiangensis showed a median estimated genome size of 3.53 Mb, the second largest of the whole L. plantarum group up to now. Lactobacillus pentosus showed the largest median estimated genome size (3.77 Mb), followed by L. mudanjiangensis (3.53 Mb) and L. fabifermentans (3.43 Mb), whereas for L. xiangfangensis (3.0 Mb) and L. herbarum (2.9 Mb) this size was much smaller. A remarkable high spread in genome length was found within strains belonging to the L. plantarum species, as their genome size ranged between 2.9 Mb and 3.8 Mb. Furthermore, L. mudanjiangensis showed a GC content of 42.9%, the lowest value within the whole L. plantarum group (FIG. 3B). Finally, regarding median gene count, similar trends were found as for the genome length, with L. pentosus showing the highest count, followed by L. mudanjiangensis and L. fabifermentans, whereas L. xiangfangensis and L. herbarum harbored the lowest numbers of genes (FIG. 3C). In total, 947,588 genes were found in the whole L. plantarum group, with an average of 3,110 genes per genome. These genes were further clustered into 8,005 different orthogroups, leading to an average count of 2,924 orthogroups per genome. The differences between these numbers was due to the fact that some genes were found in multiple copies within one genome, which clustered together in a single orthogroup. Of all these orthogroups, 2,172 were defined as core orthogroups and 5,833 as accessory orthogroups. Subsequently, the distribution of orthogroups between the different L. plantarum group members was explored (FIG. 3D). The species with the highest number of species-specific orthogroups was L. plantarum. With 2,065 species-specific orthogroups, it greatly outnumbered all other species, although this number was most probably biased, due to the higher number of sequenced genomes available for L. plantarum compared with the other L. plantarum group species. It was followed by L. mudanjiangensis (FIG. 3D) that contained 372 species-specific orthogroups and L. fabifermentans harboring 213 species-specific orthogroups. Furthermore, L. plantarum and L. pentosus shared the highest number of uniquely shared orthogroups (286), followed by the combination of L. plantarum and L. paraplantarum (219 uniquely shared orthogroups), which seemed to be in line with the phylogeny described in FIG. 1. In contrast, L. mudanjiangensis shared more unique orthogroups with the phylogenetically distant L. plantarum (166 orthogroups; FIG. 3D) than it did with the most closely related species, L. fabifermentans (59 orthogroups). To get more insights into the unique properties of L. mudanjiangensis, all 372 species-specific orthogroups were further classified using the EggNOG database (inset FIG. 3D). However, this resulted in a vast majority of orthogroups (304), classified under 'Category S: Function unkown', showing that further experimental work on functional gene validation is necessary. Besides this, most orthogroups belonged to category G (carbohydrate transport and metabolism, 14 orthogroups), followed by category M (cell wall/membrane/envelope biogenesis, 13 orthogroups).

Presence of a putative conjugative system in Lactobacillus mudanjiangensis

The second most abundant category of L. mudanjiangensis-specific orthogroups, excluding category S (function unknown), were genes related to 'cell wall, membrane, or envelope biogenesis (category M). Examination of the annotation of the genes belonging to these orthogroups did not reveal any new insights, as many of them were annotated as hypothetical proteins. Therefore, SEM was performed to screen the cell surfaces of these four strains in more detail. This analysis revealed that three of the four strains (L. mudanjiangensis DSM28402$^T$, AMBF209 and AMBF249) formed pili or fimbriae, connecting different cells to each other as well as cells to an undefined structure.

To identify the genes encoding these pili, all genome sequences of L. mudanjiangensis were screened for the presence of genes associated with these kinds of phenotypes. These included the spaCBA gene cluster, which has been linked with probiotic properties in L. rhamnosus, due to better adhesion to intestinal epithelial cells, as well as secretion systems based on pili, such as the type II and type IV secretion systems (Abby et al., 2016). In this study, no spaCBA gene cluster was found. However, further exploration revealed the presence of a conjugation system in at least three of the four L. mudanjiangensis strains examined (AMBF209, AMBF249 and DSM 284021).

Figure 4:
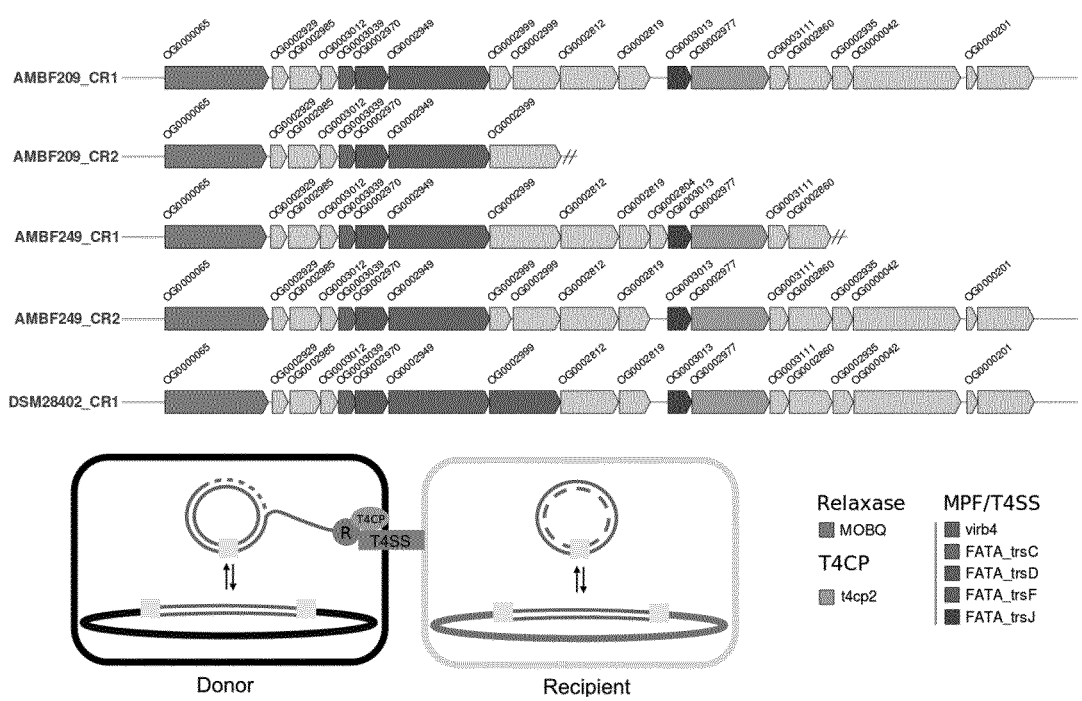
FIG. 4: Gene clusters encoding a putative conjugation system, colored by their potential function, as classified by CONJSCAN. The text above each gene shows its matching orthogroup. Schematic model representing the process of bacterial conjugation with all three mandatory elements. Scheme adapted from Guglielmini et al. (2011). (R, relaxase; T4CP, Type IV coupling protein; T4SS, Type IV secretion system).

Two complete conjugation systems containing all three mandatory parts (FIG. 4) were found in L. mudanjiangensis AMBF209 and AMBF249, whereas one complete conjugation system was found in L. mudanjiangensis DSM 28402$^T$ (FIG. 4). For all four *L. mudanjiangensis* strains, the relaxase gene of this conjugation system was classified as a member of the MOBQ class, whereas the coupling protein was classified as a T4CP2. The MPF system, which harbored the putative pilus, was further classified as belonging to the class $MPF_{FATA}$, which groups the MPF systems of Gram-positive bacteria. VirB4 was identified as the ATPase motor of this MPF system. Furthermore, this MPF system contained three accessory genes (trsC, trsD and trsJ) in *L. mudanjiangensis* AMBF209 and AMBF249, whereas four accessory genes were annotated in *L. mudanjiangensis* DSM $28402^T$ (trsC, trsD, trsFand trsJ) (FIG. 4). Homologs for the genes trsC and trsD were already previously identified, with trsC coding for a VirB3 homolog, which is linked to the formation of the membrane pore, and trsD coding for another homolog of VirB4, the conjugation ATPase. In contrast, both trsF and trsJ are poorly characterized.

Further analysis of the genes surrounding the annotated conjugation genes showed that this genomic region contained 18 to 19 open reading frames, most of them annotated as hypothetical proteins (FIG. 4). However, a bacteriophage peptidoglycan hydrolase domain was found in orthogroup OG0002812 in both *L. mudanjiangensis* AMBF209 conjugation region 1 (AMBF209_CR1) and *L. mudanjiangensis* AMBF249 conjugation region 2 (AMBF249_CR2), making it a VirB1-like protein. In *Agrobacterium tumefaciens*, the VirB1 protein provides localized lysis of the peptidoglycan cell wall to allow insertion of the T4SS. A similar domain, also known to harbor peptidoglycan lytic activity, was found in *L. mudanjiangensis* DSM28402_CR1 (orthogroup OG0002812). Finally, another conserved domain was found in all five gene regions clustered in orthogroup OG0003012, annotated as T4SS_CagC, which was shown to be a VirB2 homolog. VirB2 is the major pilus component of the type IV secretion system of *A. tumefaciens*, which is the main building block for extension and retraction of the conjugative pilus. Taken together, these results showed the presence of pili in three *L. mudanjiangensis* strains (AMBF209, AMBF249 and DSM $28402^T$), which after genomic analysis were hypothesized to be part of a conjugation system.

Finally, genome analysis of all other *L. plantarum* group members showed that, in contrast to an initial belief, the presence of a complete conjugation system was not unique to *L. mudanjiangensis*. All three necessary genes were also found in 58 of 275 *L. plantarum* strains, two of seven *L. paraplantarum* strains and four of twelve *L. pentosus* strains. In contrast, the system was completely absent in clade5a, *L. herbarum, L. xiangfangensis* and *L. fabifermentans*.

Plasmid Reconstruction from Genome Data

Figure 5:
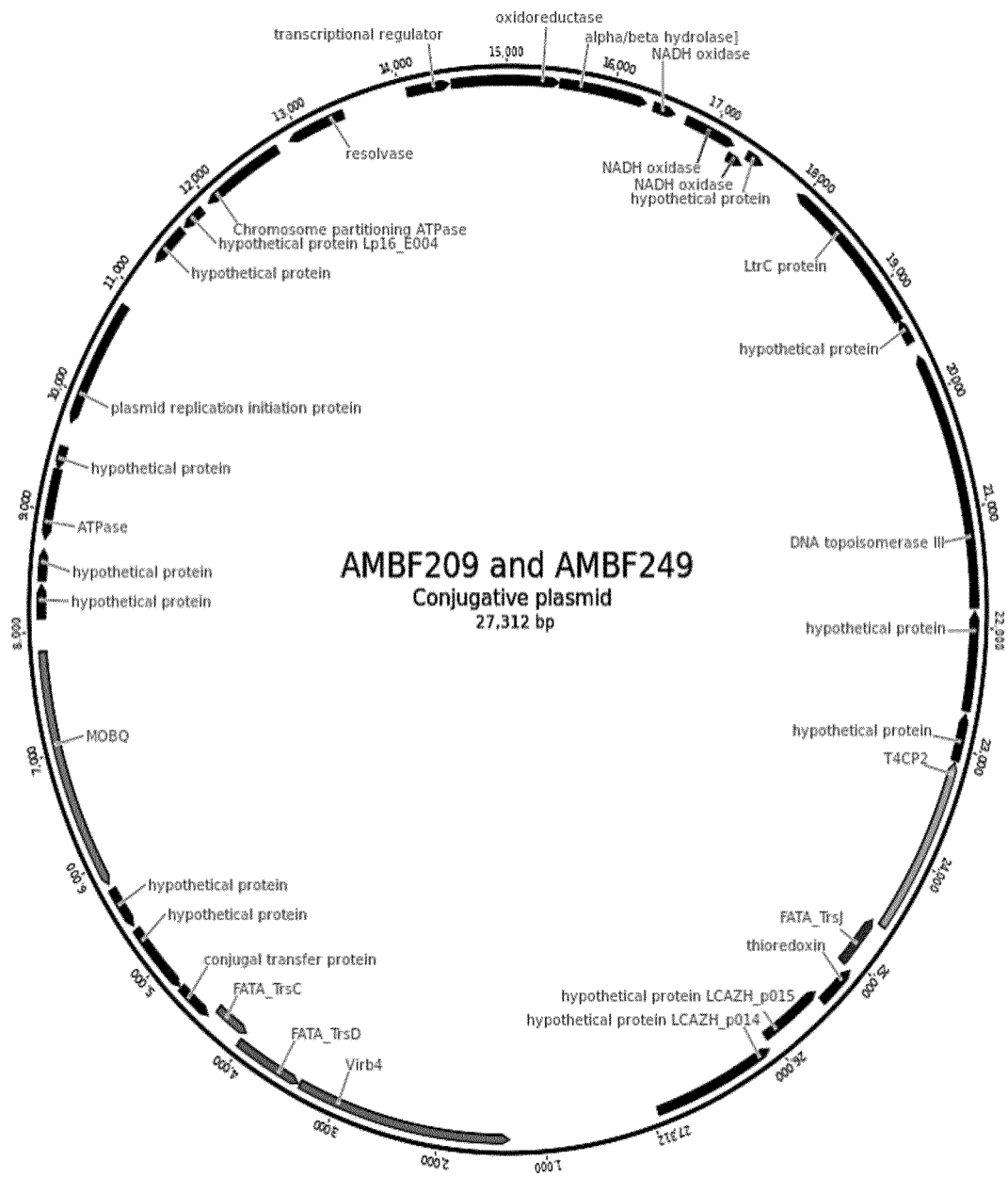
FIG. 5: Map of the predicted conjugative plasmid of *Lactobacillus mudanjiangensis* AMBF209 and AMBF249.

Many conjugation systems are coded on plasmids. Therefore, all four *L. mudanjiangensis* genomes were screened for plasmid presence using Recycler. Plasmids were only found in two of four genome assemblies, namely *L. mudanjiangensis* AMBF209 and AMBF249 (FIG. 5). Both strains harbored a plasmid of 27.3 Kb with 33 predicted genes, which after pairwise alignment of the plasmid were exactly the same. Subsequently, the presence of a conjugation system on these plasmids was confirmed using CONJScan. Further examination showed that the plasmid exactly matched the above described AMBF209_CR2 and AMBF249_CR1 gene regions (FIG. 4B). Regarding annotated genes, 13 of 33 gene products were predicted as hypothetical proteins by Prokka. Further annotation using the EggNOG database revealed that most genes were mapped to category S (function unknown), followed by category L (replication, recombination and repair) and category C (energy production and conversion). Finally, a BLAST search was performed against the NCBI nt database to explore whether a similar plasmid was already described in the literature. This resulted in a best matching hit, showing 97% identity and 76% query coverage with plasmid pKLC4 of *Leuconostoc carnosum* JB16 (GenBank accession number CP003855). This plasmid was found in a strain isolated from kimchi (Jung et al., 2012) and has a length of 36.6 Kb, indicating that some deletions occurred in the *L. mudanjiangensis* plasmids. All together, these results showed that *L. mudanjiangensis* strains AMBF209 and AMBF249 carried the same conjugative plasmid, of which the encoded gene functions are poorly characterized.

Since only two of five conjugation regions (FIG. 5) were plasmid-encoded, an additional analysis was performed to assess whether the other three conjugation systems could be part of an ICE. For this, all four *L. mudanjiangensis* genomes were analyzed similar to a recently published method (Cury et al., 2017). However, ICE regions usually contain repeats, such as transposases, leading to fragmentation of these ICE regions, if short read sequencing technology is used (Cury et al., 2017). Therefore, these analysis methods usually require a complete genome for proper ICE identification. The assembly state of the four genomes made it thus hard to correctly interpret the results obtained.

*Lactobacillus mudanjiangensis* Harbors a Potential Cellulose-Degrading Enzyme

Carbohydrate transport and metabolism (category G) was found to be the most abundantly characterized category among the *L. mudanjiangensis* species-specific orthogroups. Further examination of the 14 unique orthogroups that were detected in this category, revealed the presence of a gene in all four strains annotated as endoglucanase E1, which is involved in the conversion of cellulose polymers into simple saccharides. A BLAST search of the DNA sequences of this gene to the NCBI nt database showed a best scoring hit (26% coverage and 69% identity) with a member of the *Herbinix* species (GenBank accession number LN879430). The *Herbinix* genus contains cellulose-degrading bacteria. This result also showed that this gene was not found in any other member of the *Lactobacillus* Genus Complex (LGC), or any other LAB (*Lactococcus, Streptococcus, Bifidobacterium* . . . ), and confirmed its uniqueness to *L. mudanjiangensis*. Since endoglucanases are classified as glycosyl hydrolases (GHs), this endoglucanase E1 gene was compared to the CAZY database. Indeed, for all four strains, this gene was classified as belonging to the GH5_1 family, which was a family uniquely found in *L. mudanjiangensis*. Although this GH family showed some degree of polyspecificity, the majority of enzymes (22 of 24 enzymes characterized) are reported as endoglucanases. Together, these results thus pointed towards the presence of a novel putative cellulose-degrading enzyme in all four *L. mudanjiangensis* strains.

Characterization of the Cellulose Degrading Enzyme

In Table 2, the activity of the cellulose degrading enzyme is shown. The three *L. mudanjiangensis* strains (AMBF197, AMBF209 and AMBF249) isolated from Flemish carrot fermentations showed degradation activity of carboxymethyl cellulose (CMC). Both the cells as the lysed of three *L. mudanjiangensis* strains (AMBF197, AMBF209, and AMBF249) showed degradation of CMC, indicating its cellulase activity. The negative control (*L. plantarum* WCFS1) did not show this activity as well as the *L. mudanjiangensis* DSM $28401^T$. The cell free supernatant did not show any cellulase activity.

TABLE 2

Carboxymethyl cellulose assay of all known *L. mudanjiangensis* strains and *L. plantarum* WCFS1 reference strain. Diameter of the halos in mm show the enzyme activity semi-quantitatively. The different *L. mudanjiangensis* strains (DSM 24802$^T$, AMBF197, AMBF209 and AMBF249) and reference *L. plantarum* WCFS1 are shown. Different conditions were used: Cell = concentrated cells; CFS = Cell Free Supernatant; Lys = Lysed cells; Lys pH = Lysed cells pH adjusted to the pH of the CFS.

| Strain | Cell – halo (mm) | Lys – halo (mm) | Lys pH – halo (mm) |
|---|---|---|---|
| WCFS1 | 0 | 0 | 0 |
| DSM 28402 | 0 | 0 | 0 |
| AMBF197 | 8.3 | 8.7 | 9 |
| AMBF209 | 7.3 | 7.45 | 7.7 |
| AMBF249 | 8 | 9 | 10.5 |

The lysed cells expressing the putative cellulase showed a larger halo, indicating the activity of the heterologously expressed protein. When the pH correction to the pH of the CFS of *L. mudanjiangensis*, the mean increase was lower, but not significant. No cellulase activity was shown for the live concentrated *E. coli* cells or both the pH uncorrected and corrected cell free supernatant.

TABLE 3

Carboxymethyl cellulose assay of the heterologously expressed cellulase in *E. coli* BL21 pLysS. Increase in diameter of the halos in mm show the enzyme activity semi-quantitatively. SE is the standard error of the mean. Lys: lysate of the cellulose producing *E. coli* BL21 pLysS cells. Lys pH4: pH of the lysate was corrected to a pH of 4 to mimic the CFS of *L. mudanjiangensis*.

| | Lys | Lys pH4 |
|---|---|---|
| Mean increase halo ± SE (mm) | 1.94 ± 0.83 | 1.20 ± 0.51 |

CONCLUSION

Herein, the genome sequences of four *L. mudanjiangensis* strains were studied in relation to the closely related members of the *L. plantarum* group. Comparative genome analysis of this phylogenetic group found two wrongly annotated genome assemblies and intraclade ANI values below the commonly used species delimitation threshold for *L. plantarum* and *L. pentosus*. Furthermore, *L. mudanjiangensis* harbored one of the largest genomes and the highest gene counts of the *L. plantarum* group. Three of the four *L. mudanjiangensis* strains studied showed the presence of pili on SEM images, which were linked to conjugative gene regions. Most interestingly, a broad repertoire of GHs and a capability to degrade cellulose was shown. Therefore, a nomadic or plant-adapted lifestyle could be assigned to *L. mudanjiangensis*. Finally, the putative cellulase activity is supported by experimental indication of its carboxymethyl cellulose degrading capacity.

REFERENCES

Abby, S. S., Cury, J., Guglielmini, J., Néron, B., Touchon, M., & Rocha, E. P. C. (2016). Identification of protein secretion systems in bacterial genomes. *Scientific Reports*, 6(1), 23080.

Cury, J., Touchon, M., & Rocha, E. P. C. (2017). Integrative and conjugative elements and their hosts: composition, distribution and organization. *Nucleic Acids Research*, 45(15), 8943-8956.

Goris, J., Konstantinidis, K. T., Klappenbach, J. A., Coenye, T., Vandamme, P., & Tiedje, J. M. (2007). DNA-DNA hybridization values and their relationship to whole-genome sequence similarities. *International Journal of Systematic and Evolutionary Microbiology*, 57(Pt 1), 81-91.

Gu, C. T., Li, C. Y., Yang, L. J., & Huo, G. C. (2013). *Lactobacillus mudanjiangensis* sp. nov., *Lactobacillus songhuajiangensis* sp. nov. and *Lactobacillus nenjiangensis* sp. nov., isolated from Chinese traditional pickle and sourdough. *International Journal of Systematic and Evolutionary Microbiology*, 63(Pt 12), 4698-4706.

Guglielmini, J., Quintais, L., Garcillán-Barcia, M. P., Cruz, F. de la, & Rocha, E. P. (2011). The repertoire of ice in prokaryotes underscores the unity, diversity, and ubiquity of conjugation. *PLoS Genetics*, 7(8).

Jung, J. Y., Lee, S. H., & Jeon, C. O. (2012). Complete genome sequence of *Leuconostoc carnosum* strain JB16, isolated from kimchi. *Journal of Bacteriology*, 194(23), 6672-6673.

Liang, Y. L., Zhang, Z., Wu, M., Wu, Y. & Feng, J. X. (2014). Isolation, screening, and identification of cellulolytic bacteria from natural reserves in the subtropical region of China and optimization of cellulase production by Paenibacillus terrae ME27-1. *BioMed Research International* 2014.

Omadjela, O., Narahari, A., Strumillo, J., Mélida, H., Mazur, O., Bulone, V. & Zimmer, J. (2013). BcsA and BcsB form the catalytically active core of bacterial cellulose synthase sufficient for in vitro cellulose synthesis. *Proceedings of the National Academy of Sciences of the United States of America* 110, 17856-17861.

SEQUENCE LISTING

```
<210> 1
<211> 1263
<212> DNA
<213> Lactobacillus mudanjiangensis
<223> Cellulase Gene
<400> 1
atgaagtggc gcattgggtt gttgacactt attgcaggtt tggcactggg gagtgtcggt      60
ggtcaggcag cgagtcgacc taagagtgac tggttgcatg caaagggtaa tcgaattgtg     120
gatgcacggg gcaaaacggt tcggattacg gggttaaatt ggtttgggta taacactggg     180
accaatacgt ttgatggact atggaccgcg aacttagata agacggttaa atcggtggct     240
aatcatggat ttaatacgat tcgggtgcca ttttctgttc aattggtaaa agcttggtca     300
```

-continued

```
cagaaaaagt atcccaaggc gaacattaat ttaagtacca atgccgcttt gaagggcaaa   360
aatagtttac agatctggca acggttcttg gctgattgcc agaaaaatgg gattaaagtc   420
atcattgata tgcatagtgc caagagtgat ccacaaggcc acaatgcacc attatggaaa   480
tccggtaaat ataccactaa agactattat gcggcgttaa cttggttagc taagcgttac   540
aagaagaatg atacgatcat tggttatgac ttgaagaatg aaccacatgg tctcgtgact   600
gatgccagct atgcgaaatg ggacggctcc aaagcaagta acaactggcg ctatatcgct   660
gctcaagcgg gtaagaaagt gttgaaagct aatccgcatg cgttgatctt cgtcgaaggg   720
gttcaaagca ccccgaagag ttggaagact ggctataaga agtcagcgca atacaactac   780
acgttgtggg gtgccaactt acgtggggtc gctaaatatc cagtcaaggt gaagaagtca   840
caactggtct attcgattca tgattacggt cctagtgtgg caccagggag ctcatggtta   900
caaggtaact ttacttacaa ttcattgatg aagaactact ggcggccgaa ctggtacttt   960
attcatgcga agaagaccgc accattgtac attggtgaat ggggcggcta cttaaccggt  1020
agcaatctga aatggatgaa agctgaacgt aagttgatta cgacgcataa gttgaacttt  1080
acgttctggt gcttgaataa caactccggt gatactggtg gcttgttgaa tagcgactgg  1140
acgacttgga atagcaagtt atacaagttc gtgaaaccga ctctttggca atcgaagaag  1200
ggtcaattct acagtctaga cggtcaagtt aaattgggga ccaaaggctt acggaaacca  1260
taa                                                                1263
```

<210> 2
<211> 420
<212> PRT
<213> *Lactobacillus mudanjiangensis*
<223> Cellulase Enzyme

<400> 2

```
Met Lys Trp Arg Ile Gly Leu Leu Thr Leu Ile Ala Gly Leu Ala Leu
1               5                   10                  15

Gly Ser Val Gly Gly Gln Ala Ala Ser Arg Pro Lys Ser Asp Trp Leu
            20                  25                  30

His Ala Lys Gly Asn Arg Ile Val Asp Ala Arg Gly Lys Thr Val Arg
        35                  40                  45

Ile Thr Gly Leu Asn Trp Phe Gly Tyr Asn Thr Gly Thr Asn Thr Phe
    50                  55                  60

Asp Gly Leu Trp Thr Ala Asn Leu Asp Lys Thr Val Lys Ser Val Ala
65                  70                  75                  80

Asn His Gly Phe Asn Thr Ile Arg Val Pro Phe Ser Val Gln Leu Val
                85                  90                  95

Lys Ala Trp Ser Gln Lys Lys Tyr Pro Lys Ala Asn Ile Asn Leu Ser
            100                 105                 110

Thr Asn Ala Ala Leu Lys Gly Lys Asn Ser Leu Gln Ile Trp Gln Arg
        115                 120                 125

Phe Leu Ala Asp Cys Gln Lys Asn Gly Ile Lys Val Ile Ile Asp Met
    130                 135                 140

His Ser Ala Lys Ser Asp Pro Gln Gly His Asn Ala Pro Leu Trp Lys
145                 150                 155                 160

Ser Gly Lys Tyr Thr Thr Lys Asp Tyr Tyr Ala Ala Leu Thr Trp Leu
                165                 170                 175

Ala Lys Arg Tyr Lys Lys Asn Asp Thr Ile Ile Gly Tyr Asp Leu Lys
            180                 185                 190

Asn Glu Pro His Gly Leu Val Thr Asp Ala Ser Tyr Ala Lys Trp Asp
        195                 200                 205
```

-continued

```
Gly Ser Lys Ala Ser Asn Asn Trp Arg Tyr Ile Ala Gln Ala Gly
    210                 215                 220

Lys Lys Val Leu Lys Ala Asn Pro His Ala Leu Ile Phe Val Glu Gly
225                 230                 235                 240

Val Gln Ser Thr Pro Lys Ser Trp Lys Thr Gly Tyr Lys Lys Ser Ala
                245                 250                 255

Gln Tyr Asn Tyr Thr Leu Trp Gly Ala Asn Leu Arg Gly Val Ala Lys
                260                 265                 270

Tyr Pro Val Lys Val Lys Ser Gln Leu Val Tyr Ser Ile His Asp
            275                 280                 285

Tyr Gly Pro Ser Val Ala Pro Gly Ser Ser Trp Leu Gln Gly Asn Phe
    290                 295                 300

Thr Tyr Asn Ser Leu Met Lys Asn Tyr Trp Arg Pro Asn Trp Tyr Phe
305                 310                 315                 320

Ile His Ala Lys Lys Thr Ala Pro Leu Tyr Ile Gly Glu Trp Gly Gly
                325                 330                 335

Tyr Leu Thr Gly Ser Asn Leu Lys Trp Met Lys Ala Glu Arg Lys Leu
                340                 345                 350

Ile Thr Thr His Lys Leu Asn Phe Thr Phe Trp Cys Leu Asn Asn Asn
                355                 360                 365

Ser Gly Asp Thr Gly Gly Leu Leu Asn Ser Asp Trp Thr Thr Trp Asn
    370                 375                 380

Ser Lys Leu Tyr Lys Phe Val Lys Pro Thr Leu Trp Gln Ser Lys Lys
385                 390                 395                 400

Gly Gln Phe Tyr Ser Leu Asp Gly Gln Val Lys Leu Gly Thr Lys Gly
                405                 410                 415

Leu Arg Lys Pro
            420
```

SEQUENCE LISTING

<160> NUMBER OF SEQ ID NOS: 2

<210> SEQ ID NO 1
<211> LENGTH: 1263
<212> TYPE: DNA
<213> ORGANISM: Lactobacillus mudanjiangensis
<220> FEATURE:
<223> OTHER INFORMATION: Cellulase Gene

<400> SEQUENCE: 1

```
atgaagtggc gcattgggtt gttgacactt attgcaggtt tggcactggg gagtgtcggt    60
ggtcaggcag cgagtcgacc taagagtgac tggttgcatg caaagggtaa tcgaattgtg   120
gatgcacggg gcaaaacggt tcggattacg gggttaaatt ggtttgggta taacactggg   180
accaatacgt ttgatggact atggaccgcg aacttagata agacggttaa tcggtggct   240 aatcatggat ttaatacgat tcgggtgcca ttttctgttc aattggtaaa agcttggtca   300
cagaaaaagt atcccaaggc gaacattaat ttaagtacca atgccgcttt gaagggcaaa   360
aatagtttac agatctggca acggttcttg gctgattgcc agaaaaatgg gattaaagtc   420
atcattgata tgcatagtgc caagagtgat ccacaaggcc acaatgcacc attatggaaa   480
tccggtaaat ataccactaa agactattat gcggcgttaa cttggttagc taagcgttac   540
aagaagaatg atacgatcat tggttatgac ttgaagaatg aaccacatgg tctcgtgact   600
gatgccagct atgcgaaatg ggacggctcc aaagcaagta caactggcg ctatatcgct   660
```

```
gctcaagcgg gtaagaaagt gttgaaagct aatccgcatg cgttgatctt cgtcgaaggg    720
gttcaaagca ccccgaagag ttggaagact ggctataaga agtcagcgca atacaactac    780
acgttgtggg gtgccaactt acgtggggtc gctaaatatc cagtcaaggt gaagaagtca    840
caactggtct attcgattca tgattacggt cctagtgtgg caccagggag ctcatggtta    900
caaggtaact ttacttacaa ttcattgatg aagaactact ggcggccgaa ctggtacttt    960
attcatgcga agaagaccgc accattgtac attggtgaat ggggcggcta cttaaccggt   1020
agcaatctga aatggatgaa agctgaacgt aagttgatta cgacgcataa gttgaacttt   1080
acgttctggt gcttgaataa caactccggt gatactggtg gcttgttgaa tagcgactgg   1140
acgacttgga atagcaagtt atacaagttc gtgaaaccga ctctttggca atcgaagaag   1200
ggtcaattct acagtctaga cggtcaagtt aaattgggga ccaaaggctt acggaaacca   1260
taa                                                                 1263
```

<210> SEQ ID NO 2
<211> LENGTH: 420
<212> TYPE: PRT
<213> ORGANISM: Lactobacillus mudanjiangensis
<220> FEATURE:
<223> OTHER INFORMATION: Cellulase Enzyme

<400> SEQUENCE: 2

```
Met Lys Trp Arg Ile Gly Leu Leu Thr Leu Ile Ala Gly Leu Ala Leu
1               5                   10                  15

Gly Ser Val Gly Gly Gln Ala Ala Ser Arg Pro Lys Ser Asp Trp Leu
            20                  25                  30

His Ala Lys Gly Asn Arg Ile Val Asp Ala Arg Gly Lys Thr Val Arg
        35                  40                  45

Ile Thr Gly Leu Asn Trp Phe Gly Tyr Asn Thr Gly Asn Thr Phe
    50                  55                  60

Asp Gly Leu Trp Thr Ala Asn Leu Asp Lys Thr Val Lys Ser Val Ala
65                  70                  75                  80

Asn His Gly Phe Asn Thr Ile Arg Val Pro Phe Ser Val Gln Leu Val
                85                  90                  95

Lys Ala Trp Ser Gln Lys Lys Tyr Pro Lys Ala Asn Ile Asn Leu Ser
            100                 105                 110

Thr Asn Ala Ala Leu Lys Gly Lys Asn Ser Leu Gln Ile Trp Gln Arg
        115                 120                 125

Phe Leu Ala Asp Cys Gln Lys Asn Gly Ile Lys Val Ile Ile Asp Met
    130                 135                 140

His Ser Ala Lys Ser Asp Pro Gln Gly His Asn Ala Pro Leu Trp Lys
145                 150                 155                 160

Ser Gly Lys Tyr Thr Thr Lys Asp Tyr Tyr Ala Ala Leu Thr Trp Leu
                165                 170                 175

Ala Lys Arg Tyr Lys Lys Asn Asp Thr Ile Ile Gly Tyr Asp Leu Lys
            180                 185                 190

Asn Glu Pro His Gly Leu Val Thr Asp Ala Ser Tyr Ala Lys Trp Asp
        195                 200                 205

Gly Ser Lys Ala Ser Asn Asn Trp Arg Tyr Ile Ala Ala Gln Ala Gly
    210                 215                 220

Lys Lys Val Leu Lys Ala Asn Pro His Ala Leu Ile Phe Val Glu Gly
225                 230                 235                 240

Val Gln Ser Thr Pro Lys Ser Trp Lys Thr Gly Tyr Lys Lys Ser Ala
                245                 250                 255
```

-continued

```
Gln Tyr Asn Tyr Thr Leu Trp Gly Ala Asn Leu Arg Gly Val Ala Lys
        260                 265                 270

Tyr Pro Val Lys Val Lys Lys Ser Gln Leu Val Tyr Ser Ile His Asp
        275             280                 285

Tyr Gly Pro Ser Val Ala Pro Gly Ser Ser Trp Leu Gln Gly Asn Phe
        290             295                 300

Thr Tyr Asn Ser Leu Met Lys Asn Tyr Trp Arg Pro Asn Trp Tyr Phe
305             310                 315                 320

Ile His Ala Lys Lys Thr Ala Pro Leu Tyr Ile Gly Glu Trp Gly Gly
            325                 330                 335

Tyr Leu Thr Gly Ser Asn Leu Lys Trp Met Lys Ala Glu Arg Lys Leu
            340                 345                 350

Ile Thr Thr His Lys Leu Asn Phe Thr Phe Trp Cys Leu Asn Asn Asn
            355                 360                 365

Ser Gly Asp Thr Gly Gly Leu Leu Asn Ser Asp Trp Thr Thr Trp Asn
    370                 375                 380

Ser Lys Leu Tyr Lys Phe Val Lys Pro Thr Leu Trp Gln Ser Lys Lys
385                 390                 395                 400

Gly Gln Phe Tyr Ser Leu Asp Gly Gln Val Lys Leu Gly Thr Lys Gly
                405                 410                 415

Leu Arg Lys Pro
            420
```

The invention claimed is:

1. A cultured host cell containing a recombinant nucleic acid molecule comprising a nucleotide sequence having at least 95% sequence identity to the nucleotide sequence of SEQ ID NO: 1, and encoding a polypeptide having cellulase activity; wherein the recombinant nucleic acid molecule is heterologous to the host cell.

2. The cultured host cell containing the recombinant nucleic acid molecule as defined in claim 1, encoding a polypeptide comprising an amino acid sequence having at least 95% sequence identity to the amino acid sequence of SEQ ID NO: 2.

3. A method for degrading cellulose, the method comprising:
    growing an isolated bacterial strain of a *Lactobacillus mudanjiangensis* species comprising a nucleotide sequence having at least 95% sequence identity to the nucleotide sequence of SEQ ID NO: 1 in a culture medium;
    extracting a cell-free supernatant from the culture medium;
    contacting a sample comprising cellulose with the cell-free supernatant, whereby the cellulose in the sample is degraded.

4. The method according to claim 3, further comprising sterilizing the cell-free supernatant prior to the contacting step.

5. The method according to claim 3, wherein the sample comprising cellulose is selected from the group consisting of soil, wine, beer, fruit pomace, vegetable pomace, fruit juice, fruit puree, paper pulp, and textile fibers.

6. The method according to claim 3, wherein the nucleotide sequence encodes a polypeptide comprising an amino acid sequence having at least 95% sequence identity to the amino acid sequence of SEQ ID NO: 2.

7. The method according to claim 3, wherein the *Lactobacillus mudanjiangensis* species is deposited as *Lactobacillus mudanjiangensis* AMBF249 under accession number LMG P-31215.

* * * * *